United States Patent
Farmer

(10) Patent No.: US 6,264,887 B1
(45) Date of Patent: *Jul. 24, 2001

(54) AIR FRESHENING DEVICE FOR AUTOMOBILES

(76) Inventor: Mike Farmer, 4604 Deerfield Ct., Sioux Falls, SD (US) 57105

(*) Notice: Subject to any disclaimer, the term of this patent is extended or adjusted under 35 U.S.C. 154(b) by 0 days.

This patent is subject to a terminal disclaimer.

(21) Appl. No.: 09/556,707

(22) Filed: Apr. 24, 2000

Related U.S. Application Data

(60) Division of application No. 08/857,518, filed on May 16, 1997, now Pat. No. 6,123,906, which is a continuation-in-part of application No. 08/633,125, filed on Apr. 16, 1996, now abandoned.

(51) Int. Cl.$^7$ .............................................. A61L 9/12
(52) U.S. Cl. .............................. 422/5; 422/123; 422/124; 239/36; D23/366
(58) Field of Search ................................ 422/5, 124, 123; 428/905; 424/76.3, 76.4; 239/60

(56) References Cited

U.S. PATENT DOCUMENTS

| | | |
|---|---|---|
| D. 281,102 | 10/1985 | Bush et al. . |
| D. 313,274 | 12/1990 | Peterson . |
| D. 365,392 | 12/1995 | VanGundy et al. . |
| D. 373,626 | 9/1996 | Dente et al. . |
| D. 382,050 | 8/1997 | Hayes . |
| D. 417,727 | 12/1999 | Christianson . |
| 2,560,681 | 7/1951 | Berkowitz . |
| 2,721,098 | 10/1955 | Mangels . |
| 2,806,315 | 9/1957 | Kalensky . |
| 3,185,394 | 5/1965 | Farrell . |
| 3,733,016 | 5/1973 | Rood . |
| 4,432,938 | 2/1984 | Meetze, Jr. . |
| 4,523,870 | 6/1985 | Spector . |
| 4,582,638 | 4/1986 | Furuuchi et al. . |
| 4,802,626 | 2/1989 | Forbes et al. . |
| 4,808,347 | 2/1989 | Dawn . |
| 4,813,344 | 3/1989 | Greif . |
| 4,840,773 | 6/1989 | Wade . |
| 4,892,711 | 1/1990 | Tendick, Sr. . |
| 4,903,584 | 2/1990 | Styles . |
| 5,269,723 | 12/1993 | Bender . |
| 5,273,690 | 12/1993 | McDowell . |
| 5,368,822 | 11/1994 | McNeil . |
| 5,407,642 | 4/1995 | Lord . |
| 5,422,078 | 6/1995 | Colon . |
| 5,478,505 | 12/1995 | McElfresh et al. . |
| 5,527,493 | 6/1996 | McElfresh et al. . |
| 5,547,636 | 8/1996 | Vick et al. . |
| 5,603,455 | 2/1997 | Lin . |
| 5,762,549 | 6/1998 | Scheuer et al. . |
| 5,772,959 | 6/1998 | Bermas . |
| 5,775,876 | 7/1998 | Walker . |
| 5,833,929 | 11/1998 | Watson et al. . |
| 5,932,147 | 8/1999 | Chen . |
| 6,123,906 * | 9/2000 | Farmer ...................... 422/124 |

* cited by examiner

Primary Examiner—Elizabeth McKane
(74) Attorney, Agent, or Firm—Fulwilder Patton Lee & Utecht, LLP

(57) ABSTRACT

A device for allowing either perfumed materials or deodorizing materials to the surrounding air of a vehicle, includes a clip device adapted to be connected to an air vent fin. The device is adapted to be inserted into the vent where it will be less intrusive into space outside the vent.

17 Claims, 1 Drawing Sheet

AIR FRESHENING DEVICE FOR AUTOMOBILES

This application is a divisional of Ser. No. 08/587,518 filed May 16, 1997, now U.S. Pat. No. 6,123,906, which is a continuation in part of applicants prior application, Ser. No. 08/633,125, filed Apr. 16, 1996 and now specifically abandoned.

BACKGROUND OF THE INVENTION

This invention pertains to air fresheners adapted to remove or to cover unpleasant odors in some living space. It is adapted for use in automotive vehicles or in dwellings and includes a novel clip device adapted to be held in the discharge of a heating or a cooling system.

DESCRIPTION OF PRIOR ART

In many types of living space, but particularly in the passenger compartment of cars and trucks, there are often unpleasant odors. Such odors as that of stale tobacco smoke or odors of some material being carried in the passenger compartment can be offensive to many people. Often that offensive odor is opposed by use of hanging devices having other perfumes or deodorant material absorbed into the device to be hung in the car. These devices are most often hung from the rear-view mirror or the sun shades in the vehicle.

This invention provides a simple and much more efficient way of distributing the sort of material that is absorbed into the former hanging devices. It also avoids any dangling object which might be distracting to the driver of an automobile. Further, it is inserted to be non-intrusive in outer space.

The need for an inexpensive and convenient to use air freshener to take advantage of forced air in an air grill has long been recognized. It has been proposed to provide an automobile air vent with wide spaced louvers for receipt thereon of a releasable fastener so that a container containing a deodorant may be mounted therefrom. A device of this type is shown in U.S. Pat. No. 4,813,344 to Greif. Devices of this type suffer the shortcoming that they are relatively cumbersome, expensive to manufacture and require a separate clip type fastener or the like for mounting purposes.

Many different deodorant containers have been proposed with separate mounting clips to facilitate mounting of the containers to a grill, louver or the like for reduced flow through passages or orifices in the container for enhancing release of the deodorant material. Examples of these devices are shown in prior U.S. Pat. No. 4,480,773 to Wade and U.S. Pat. No. 5,547,636 to Vick et al. and assigned to New Ideas International, Inc. The Wade device shows a container defining a compartment while the Vick device shows a sheet segment of polyurethane foam having a solid residue for emitting fragrance and secured to a filter by means of an arrow shaped mounting device.

It has also been proposed to provide an air freshener constructed with a plurality of separable pods or fingers having a plurality of storing cells held between breakable walls and connectable by means of tethering hooks to a vent, louver or the like to be suspended freely in the air flow passing through openings between such louvers. A device of this type is shown in U.S. Pat. No. 5,273,690 to McDowell. It has also been proposed that such a device could be mounted in an air filter behind a screen or the like. Devices of this type, while acceptable for their intended purposes, suffer the shortcoming that they are not conveniently and easily mounted in relatively fixed relationship within the air passage formed between the louvers.

SUMMARY OF THE INVENTION

The present invention is characterized by a method of making and using a fragrance impregnated air freshener formed from a stock of impregnated material, configured to be received bodily between transversely projecting louvers for flow thereover of the air passage and configured to be mounted directly to one or more of the louvers to be held in the desired position.

The method of making the device involves selecting a stock of impregnated material and forming it in such a configuration as to be received between the louvers and to form a mouth connectable to one or more of the louvers. The invention first involves a method of using the device by placing it in the space between respective louvers and positioning it for flow therepast either in a parallel or diagonal direction.

DESCRIPTION

Figure 1:
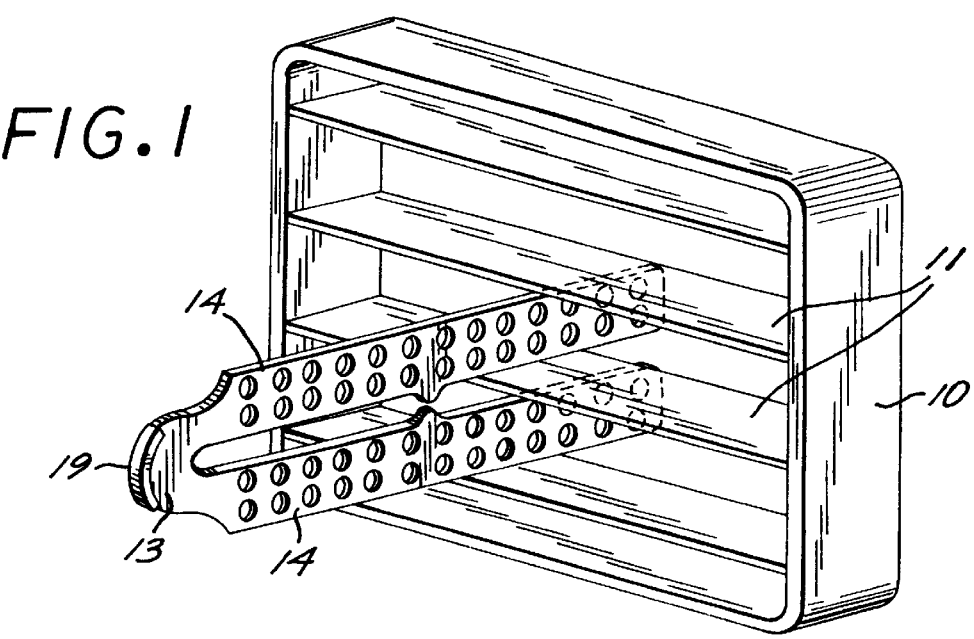
FIG. 1 is a perspective view of the air freshener clip in place on a discharge grill.
Figure 2:
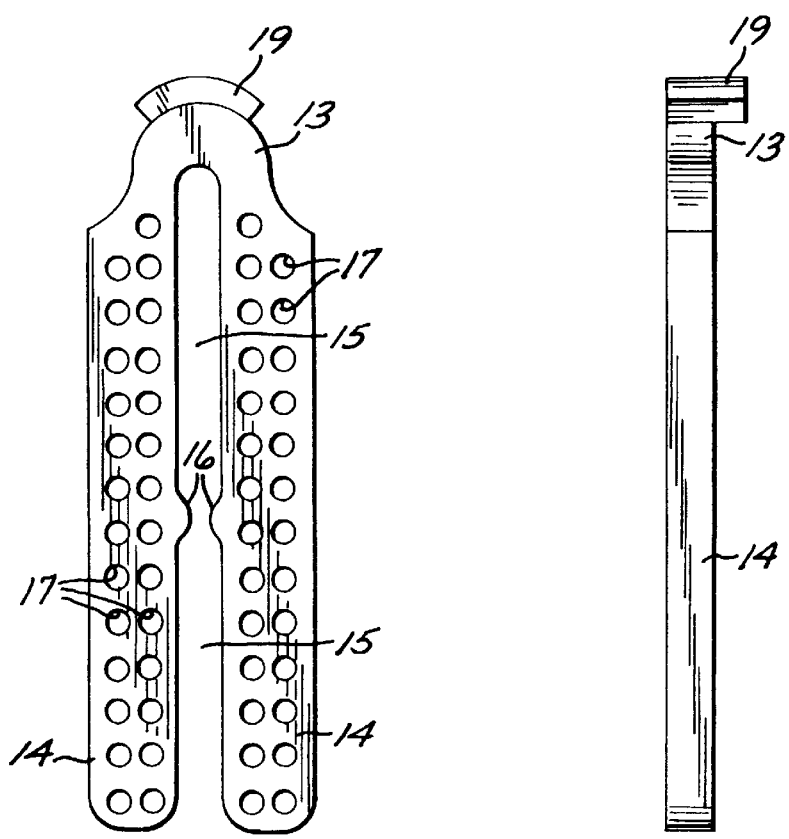
FIG. 2 is a plan view of the clip to an enlarged scale.
Figure 3:
FIG. 3 is an edge view of the clip shown in FIG. 2.

Briefly this invention is a clip adapted to carry a deodorant or perfumed material and adapted by its formation to be held directly in the flow of air from a vent whether that air is heated or cooled.

More specifically, and referring to the drawings, the clip is designed principally to be held in a discharge vent 10 of a ventilation system but it may also be adapted to any similar vent of any ventilating mechanism such as a central heater or air conditioner or a room air conditioner or other similar system which has louvers 11 in the discharge.

The clip itself is shaped as a flat sheet of a polypropylene polymer material impregnated at forming with an oil having the desired fragrance. Such materials are generally known and are often used in the form of small cakes for use in urinals in men's public restrooms. In essence the clip is shaped as a fork having a head end 13 and two legs 14. The legs are spaced apart so as to leave spaces 15 between them, but also carry matching, opposite protrusions 16 which are adapted almost to close the spaces 15. Thus, while the legs 14 are wide enough that they cannot easily be spread, there is space enough in the open spaces 15 to receive the louvers 11, of the vent.

The legs fit between the louvers, so that the clip can then be inserted into place. The natural resilience of the material of the clip allows the protrusion to slide over the louvers 11 and may thus hold the clip in place.

Tranverse holes 17 are provided to provide laterally projecting surfaces to increase the area from which the fragrance impregnated into the polypropylene material will be emitted. If the clip is placed somewhat diagonal to the airflow, the flow of air through these holes will greatly enhance the effectiveness of the device.

For ease in handling, a cross tab 19 may be provided to make placement and removal of the clip easier.

I claim as my invention:

1. An air freshener clip apparatus for mounting to an automobile air grill having louvers spaced laterally apart to form air passages therebetween for flow of forced air and comprising:

a first polymer leg insertable into such passage and having proximal and free extremities, at least a portion of such leg fabricated from a polymer impregnated with a fragrance and arranged to have, when inserted, at least on longitudinal surface exposed along its length to such forced air and including transversely extending through holes spaced along the length of such portion and opening into such surface to provide hole surface for release of such fragrance;

a second elongated leg having proximal and distal extremities and connected on its proximal extremity with the proximal extremity of such first leg, projecting parallel thereto, and cooperating therewith to form between such legs a space for receipt of one such louvers;

a clip protrusion on the inside of one such legs spaced longitudinally from such proximal extremities and projecting toward the other leg to clip behind such one of such louvers;

at least one of such legs being resilient so the free extremity thereof may be flexed away from the other leg for receipt of such one louver past such protrusion into such space to position such protrusion behind such louver to cooperate in holding the first and second legs in position on such louver; and a cross tab on the proximal extremity of such clip and projecting laterally of such legs to be grasped for insertion and removal of such clip.

2. The air freshener clip as set forth in claim 1 wherein: the first and second legs are integral.

3. The air freshener clip as set forth in claim 1 wherein: the first and second legs are one piece.

4. The air freshener clip as set forth in claim 1 wherein: at least one of such legs is constructed of polypropylene.

5. An air freshener clip apparatus for mounting to an automobile air grill having louvers spaced apart to form air passages therebetween for low of forced air, comprising:

first and second legs insertable into passages on the opposite sides of one of such louvers and formed with proximal ends connected together and projecting parallel to one another in spaced apart relationship to form a space therebetween for receipt of such louver;

one of such legs including a portion projecting toward the other of such legs and configured to, when such louver is received in such space, register behind one of such louvers and to cooperate with the other leg to hold such clip apparatus on such louver;

at least a portion of one such legs fabricated from a fragrance emitting polymer impregnated with a fragrance and arranged to be, when such clip apparatus is mounted on such louver with the louver in such space, disposed in such forced air flow of air therealong, such fragrance emitting portion further being formed along the length thereof with fragrance release enhancing openings for increasing the surface of such portion as exposed to such forced air for enhancing the release of such fragrance; and a laterally projecting hand grasp at the proximal extremity of such legs.

6. A method of delivering fragrance to a climate controlled compartment formed by walls having at least one vent formed by parallel louvers spaced apart to define air passages for introduction of forced air including the following steps:

selecting an air freshener including first and second legs having a space therebetween for straddling one of such louvers with at least one of the legs including an elongated portion fabricated from a polymer having an elongated side surface and configured with fragrance release enhancing openings spaced along the length thereof and opening to at least such surface, the legs being configured to be received in such air passages;

placing the first and second legs in position in air passages on opposite sides of a selected louver to project laterally of the louvers exposing such surface for flow of such forced air along such surface over such openings to enhance the release of the impregnated fragrance; and mounting such freshener with such first and second legs in such position.

7. The method of claim 6 wherein:

the step of selecting said freshener includes selecting the type formed with a body having an open ended longitudinal slit defining such space; and the mounting step includes positioning the freshener with the at least one louver received in the slit.

8. The method of claim 6 wherein:

the mounting step includes gripping such louver between such legs.

9. The method of claim 6 wherein:

the mounting step includes mounting such freshener projecting diagonal to the direction of air flow through such passage.

10. The method of claim 6 wherein:

selecting such air freshener with such legs formed of one piece.

11. The method of claim 6 wherein:

the mounting step includes gripping said louver directly between such legs.

12. An air freshener for mounting an air grill having elongated louvers spaced laterally apart a predetermined distance to define air passages therebetween for flow of forced air and comprising:

first and second elongated legs connected together on their proximal extremities and configured to be projected into air passages on opposite sides of one of such louvers, at least a portion of one such legs including a portion fabricated from a fragrance enhancing material having an elongated exposed surface for flow of such forced air therealong;

such legs being configured with a space therebetween for receipt of such one louver to be releasably mounted therein;

at least one of such legs being resilient so the free extremity thereof can be flexed away from the other leg to facilitate mounting on such one of such louvers; and a hand grasp on the proximal extremities of such legs.

13. The air freshener clip as set forth in claim 12 wherein: a portion of one such legs projects towards the other of such leg to cooperate in releasably engaging behind such one louver.

14. The air freshener clip as set forth in claim 12 wherein: such hand grasp projects laterally of such legs.

15. The air freshener clip as set forth in claim 12 wherein: such portion includes openings spaced therealong.

16. The air freshener clip as set forth in claim 12 wherein: at least one of such legs is constructed of a polymer.

17. The air freshener clip as set forth in claim 12 wherein: such portion is constructed of a polymer.

* * * * *

UNITED STATES PATENT AND TRADEMARK OFFICE
CERTIFICATE OF CORRECTION

PATENT NO. : 6,264,887 B1
DATED : July 24, 2001
INVENTOR(S) : Mike Farmer

It is certified that error appears in the above-identified patent and that said Letters Patent is hereby corrected as shown below:

Column 3,
Line 5, replace "on" with -- one --.
Line 8, replace "hole surface for" with -- hole surfaces for --.

Signed and Sealed this

Twenty-ninth Day of January, 2002

Attest:

JAMES E. ROGAN
*Director of the United States Patent and Trademark Office*

*Attesting Officer*